United States Patent
Iannotti et al.

(10) Patent No.: US 9,033,990 B2
(45) Date of Patent: May 19, 2015

(54) DIRECTED STRUCTURE PLACEMENT GUIDE

(71) Applicants: Joseph P. Iannotti, Strongsville, OH (US); Wael K. Barsoum, Bay Village, OH (US); Jason A. Bryan, Avon Lake, OH (US)

(72) Inventors: Joseph P. Iannotti, Strongsville, OH (US); Wael K. Barsoum, Bay Village, OH (US); Jason A. Bryan, Avon Lake, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 167 days.

(21) Appl. No.: 13/859,831

(22) Filed: Apr. 10, 2013

(65) Prior Publication Data

US 2013/0267958 A1 Oct. 10, 2013

Related U.S. Application Data

(60) Provisional application No. 61/622,348, filed on Apr. 10, 2012.

(51) Int. Cl.
*A61B 17/17* (2006.01)
*A61B 19/00* (2006.01)

(52) U.S. Cl.
CPC .............. *A61B 19/46* (2013.01); *A61B 17/17* (2013.01); *A61B 17/1739* (2013.01); *A61B 17/1746* (2013.01); *A61B 2017/1778* (2013.01); *A61B 2019/467* (2013.01)

(58) Field of Classification Search
CPC ................. A61B 17/1746; A61B 2017/1778
USPC ........ 606/87, 96–98, 104; 408/241 G, 115 R, 408/115 B
See application file for complete search history.

(56) References Cited

U.S. PATENT DOCUMENTS

| | | | | |
|---|---|---|---|---|
| 550,767 | A | * 12/1895 | Thielscher | ............... 408/97 |
| 2,697,433 | A | * 12/1954 | Zehnder | ............... 606/96 |
| 2,903,920 | A | * 9/1959 | Blecha | ............... 408/115 R |
| 3,017,887 | A | 1/1962 | Heyer | |
| 3,055,370 | A | 9/1962 | McKinney et al. | |

(Continued)

FOREIGN PATENT DOCUMENTS

| | | |
|---|---|---|
| DE | 0613658 A1 | 5/1993 |
| EP | 0613658 A1 | 9/1994 |
| WO | 2011110374 A1 | 9/2011 |

OTHER PUBLICATIONS

PCT International Search Report and Written Opinion mailed Sep. 9, 2013, pp. 1-17.

*Primary Examiner* — Michael T Schaper
(74) *Attorney, Agent, or Firm* — Tarolli, Sundheim, Covell & Tummino LLP

(57) ABSTRACT

A directed structure placement guide assists with positioning at least one directed structure in at least one of a predetermined insertion trajectory and a predetermined insertion location with respect to a patient tissue surface during preparation of the patient tissue surface to receive an implant. The implant has a tissue-contacting surface. A guide base has a distal base surface mimicking the structure of at least a portion of a tissue-contacting surface of the implant. The guide base also has a proximal base surface longitudinally spaced from the proximal base surface. At least one insertion guiding structure is movably supported by the guide base and is adjustable into a guiding configuration in which at least one of the predetermined insertion trajectory and the predetermined insertion location is selectively imparted to the directed structure.

19 Claims, 15 Drawing Sheets

(56) References Cited

U.S. PATENT DOCUMENTS

| | | | |
|---|---|---|---|
| 3,115,140 A | 12/1963 | Volkman | |
| 3,282,132 A * | 11/1966 | Neuschotz | 408/115 B |
| 4,809,694 A | 3/1989 | Ferrara | |
| 5,263,956 A * | 11/1993 | Nobles | 606/130 |
| 5,354,283 A | 10/1994 | Bark et al. | |
| 5,752,962 A * | 5/1998 | D'Urso | 606/130 |
| 5,810,712 A * | 9/1998 | Dunn | 600/114 |
| 6,018,094 A * | 1/2000 | Fox | 606/191 |
| 6,110,182 A | 8/2000 | Mowlai-Ashtiani | |
| 6,117,143 A * | 9/2000 | Hynes et al. | 606/130 |
| 6,267,770 B1 * | 7/2001 | Truwit | 606/130 |
| 7,637,915 B2 | 12/2009 | Parmer et al. | |
| 7,887,544 B2 * | 2/2011 | Tornier et al. | 606/96 |
| 8,002,799 B2 | 8/2011 | Chin et al. | |
| 8,192,445 B2 * | 6/2012 | Parmer et al. | 606/130 |
| 8,628,530 B2 * | 1/2014 | Hajianpour | 606/54 |
| 2003/0040753 A1 * | 2/2003 | Daum et al. | 606/96 |
| 2003/0083667 A1 * | 5/2003 | Ralph et al. | 606/96 |
| 2004/0210217 A1 * | 10/2004 | Baynham et al. | 606/61 |
| 2004/0230197 A1 | 11/2004 | Tornier et al. | |
| 2006/0122605 A1 * | 6/2006 | Suh et al. | 606/69 |
| 2009/0228016 A1 * | 9/2009 | Alvarez | 606/88 |
| 2011/0106095 A1 | 5/2011 | Cross et al. | |
| 2013/0184707 A1 * | 7/2013 | Mirza et al. | 606/59 |

* cited by examiner

DIRECTED STRUCTURE PLACEMENT GUIDE

RELATED APPLICATION

This application claims priority from U.S. Provisional Application No. 61/622,348, filed 10 Apr. 2012, the subject matter of which is incorporated herein by reference in its entirety.

TECHNICAL FIELD

The present invention relates to an apparatus and method for use of a directed structure placement guide and, more particularly, to a directed structure placement guide for assisting with positioning at least one directed structure in at least one of a predetermined insertion trajectory and a predetermined insertion location with respect to a patient tissue surface.

BACKGROUND OF THE INVENTION

In the installation of a prosthetic shoulder joint into a patient's body, a glenoid component is implanted into the glenoid vault of the patient's scapula. An obverse surface of the glenoid component is configured for articulating contact with a humeral component carried by the patient's humerus. A reverse surface of the glenoid component is secured to the bone surface of the glenoid vault.

Because the shoulder prosthesis is normally provided to correct a congenital or acquired defect of the native shoulder joint, the glenoid vault often exhibits a pathologic, nonstandard anatomic configuration. A surgeon must compensate for such pathologic glenoid vault anatomy when implanting the glenoid component in striving to achieve a solid anchoring of the glenoid component into the glenoid vault. Detailed preoperative planning, using two- or three-dimensional internal images of the shoulder joint, often assists the surgeon in compensating for the patient's anatomical limitations. During the surgery, an elongated pin may be inserted into the surface of the patient's bone, at a predetermined trajectory and location, to act as a passive landmark or active guiding structure in carrying out the preoperatively planned implantation. This "guide pin" may remain as a portion of the implanted prosthetic joint or may be removed before the surgery is concluded. This type of pin-guided installation is common in any joint replacement procedure—indeed, in any type of surgical procedure in which a surgeon-placed fixed landmark is desirable. In much the same manner as the guide pin is placed, the patient's bone surface may be pre-drilled to accept a fastener to help affix an implant component to the patient's bone, or a self-tapping fastener may be inserted into the bone without a predrilled hole. Another optional surgical task which involves guiding placement of a landmark upon the patient's bone is the inscription of a line or point upon the patient's bone through the use of a marking device, such as an ink pen, marker, or bovie/burner. In each of these situations, a directed structure—a guide pin, a drilling tool, a fastener, and/or a marking device—may need to be guided into association with the patient's bone at a desired insertion location and/or insertion trajectory.

In addition, and again in any type of surgical procedure, modern minimally invasive surgical techniques may dictate that only a small portion of the bone or other tissue surface being operated upon is visible to the surgeon. Depending upon the patient's particular anatomy, the surgeon may not be able to precisely determine the location of the exposed area relative to the remaining, obscured portions of the bone through mere visual observation. Again, a guide pin, marking, or other landmark may be temporarily or permanently placed into the exposed bone surface to help orient the surgeon and thereby enhance the accuracy and efficiency of the surgical procedure.

A carefully placed guide pin or other landmark, bone-preparation tool, and/or fastener, regardless of the reason provided, will reduce the need for intraoperative imaging in most surgical procedures and should result in decreased operative time and increased positional accuracy, all of which are desirable in striving toward a positive patient outcome.

SUMMARY OF THE INVENTION

In an embodiment of the present invention, a directed structure placement guide is provided for assisting with positioning at least one directed structure in at least one of a predetermined insertion trajectory and a predetermined insertion location with respect to a patient tissue surface. A guide base has longitudinally opposed proximal and distal base surfaces and a plurality of coarse location apertures extending longitudinally between the proximal and distal base surfaces. Each coarse location aperture substantially corresponds to a desired coarse location for the directed structure with respect to the patient tissue surface. The distal base surface is substantially located nearer to the patient tissue surface than is the proximal base surface. A plurality of guide spheres are provided, each guide sphere having a guide bore extending therethrough and defining a trajectory path substantially longitudinally therethrough. Each guide sphere corresponds with a different selected coarse location aperture, and each guide sphere is movable with respect to the coarse location aperture to intersect the trajectory path with the coarse location aperture at a desired fine location. The desired fine location is indicative of the predetermined insertion location of the directed structure into the patient tissue surface. A guide retainer has a plurality of retainer apertures. Each retainer aperture corresponds with a different selected guide sphere. The guide spheres are substantially longitudinally interposed between the guide base and the guide retainer. The guide retainer is longitudinally movable between loose and tight retainer positions. The guide retainer exerts longitudinal compressive force upon the guide spheres when in the tight retainer position to maintain position of the guide spheres with respect to the guide base. Each guide sphere is manipulated to place the trajectory path into the predetermined insertion trajectory at the desired fine location before the guide retainer achieves the tight retainer position and the guide bore guides a directed structure passed therethrough into contact with the patient tissue surface at the predetermined insertion trajectory and location.

In an embodiment of the present invention, a directed structure placement guide is provided for assisting with positioning at least one directed structure in at least one of a predetermined insertion trajectory and a predetermined insertion location with respect to a patient tissue surface during preparation of the patient tissue surface to receive an implant. The implant has a tissue-contacting surface and a plurality of fastener apertures associated therewith. A guide base has a distal base surface mimicking the structure of at least a portion of a tissue-contacting surface of the implant. The guide base also has a proximal base surface longitudinally spaced from the distal base surface. A plurality of coarse location apertures extend through the guide base between the proximal and distal base surfaces. Each coarse location aperture bears a corresponding relationship to the guide base as does a selected fastener aperture to the implant. A plurality of guide spheres are provided. Each guide sphere has a guide bore extending therethrough and is configured to slidably and guidingly accept a directed structure. Each guide sphere is associated with a selected coarse location aperture. Each guide bore defines a trajectory path therethrough. Each guide sphere is manipulable to precess the trajectory path within a substantially conical area located longitudinally distally of the distal base surface. The conical area has an apex located at least one of within and proximal to the selected coarse location aperture. A guide retainer is located longitudinally proximally of the proximal base surface. The guide retainer is longitudinally movable between a loose retainer position, in which the plurality of guide spheres can be moved with respect to the guide base, and a tight retainer position, in which the plurality of guide spheres are substantially prevented from movement with respect to the guide base by longitudinally compressive force exerted by the guide retainer. Each guide sphere is manipulated to place a respective trajectory path into the predetermined insertion trajectory and at least one of the guide base and each guide sphere is manipulated to place a respective trajectory path into an interception position at the predetermined insertion location upon the patient tissue surface when the distal guide base is in contact with at least a portion of an underlying patient tissue surface. The guide retainer is moved from the loose retainer position to the tight retainer position to maintain each guide sphere with the trajectory path in the predetermined insertion trajectory and interception position. The guide bore is configured to slidingly accept the directed structure and to guide the directed structure into contact with the patient tissue surface at the predetermined insertion location and at the predetermined insertion trajectory.

In an embodiment of the present invention, a method of preparing a patient tissue surface to receive an implant is provided. The implant has a tissue-contacting surface and a plurality of fastener apertures associated therewith. A directed structure placement guide is provided for assisting with positioning at least one directed structure in at least one of a predetermined insertion trajectory and a predetermined insertion location with respect to the patient tissue surface during preparation of the patient tissue surface to receive the implant. The guide includes a guide base having a distal base surface mimicking the structure of at least a portion of a tissue-contacting surface of the implant. The guide base also has a proximal base surface longitudinally spaced from the distal base surface and a plurality of coarse location apertures extending through the guide base between the proximal and distal base surfaces. Each coarse location aperture bears a corresponding relationship to the guide base as does a selected fastener aperture to the implant. A plurality of guide spheres are provided, each guide sphere having a guide bore extending therethrough and configured to slidably and guidingly accept a directed structure. Each guide sphere is associated with a selected coarse location aperture. Each guide bore defines a trajectory path therethrough. Each guide sphere is manipulable to precess the trajectory path within a substantially conical area located longitudinally distally of the distal base surface. The conical area has an apex located at least one of within and proximal to the selected coarse location aperture. A guide retainer is located longitudinally proximally of the proximal base surface. The guide retainer is longitudinally movable between a loose retainer position, in which the plurality of guide spheres can be moved with respect to the guide base, and a tight retainer position, in which the plurality of guide spheres are substantially prevented from movement with respect to the guide base by longitudinally compressive force exerted by the guide retainer. Each guide sphere is manipulated to place a respective trajectory path into the predetermined insertion trajectory. At least one of the guide base and each guide sphere is manipulated to place a respective trajectory path into an interception position at the predetermined insertion location upon the patient tissue surface when the distal guide base is in contact with at least a portion of an underlying patient tissue surface. The guide retainer is moved from the loose retainer position to the tight retainer position to maintain each guide sphere with the trajectory path in the predetermined insertion trajectory and interception position. The guide bore slidingly accepts the directed structure and guides the directed structure into contact with the patient tissue surface at the predetermined insertion location and at the predetermined insertion trajectory. The patient tissue surface is penetrated with the directed structure at the predetermined insertion location and at the predetermined insertion trajectory to create an aperture in the patient tissue surface. The aperture configuration is based upon a preoperatively determined plan to install the implant into a predetermined implant orientation with respect to the patient tissue surface.

In an embodiment of the present invention, a directed structure placement guide is provided for assisting with positioning at least one directed structure in at least one of a predetermined insertion trajectory and a predetermined insertion location with respect to a patient tissue surface during preparation of the patient tissue surface to receive an implant. The implant has a tissue-contacting surface. A guide base has a distal base surface mimicking the structure of at least a portion of a tissue-contacting surface of the implant. The guide base also has a proximal base surface longitudinally spaced from the proximal base surface. At least one insertion guiding structure is movably supported by the guide base and is adjustable into a guiding configuration in which at least one of the predetermined insertion trajectory and the predetermined insertion location is selectively imparted to the directed structure. The distal base surface of the guide is placed into contact with the patient tissue surface in a substantially identical guiding orientation to an installation orientation in which the implant is affixed to the patient tissue surface and, when the distal base surface is in the guiding orientation, the insertion guiding structure guides the directed structure into contact with the patient tissue surface in at least one of the predetermined insertion location and the predetermined insertion trajectory.

BRIEF DESCRIPTION OF THE DRAWINGS

For a better understanding of the invention, reference may be made to the accompanying drawings, in which.

DESCRIPTION OF EMBODIMENTS

Figure 1A:
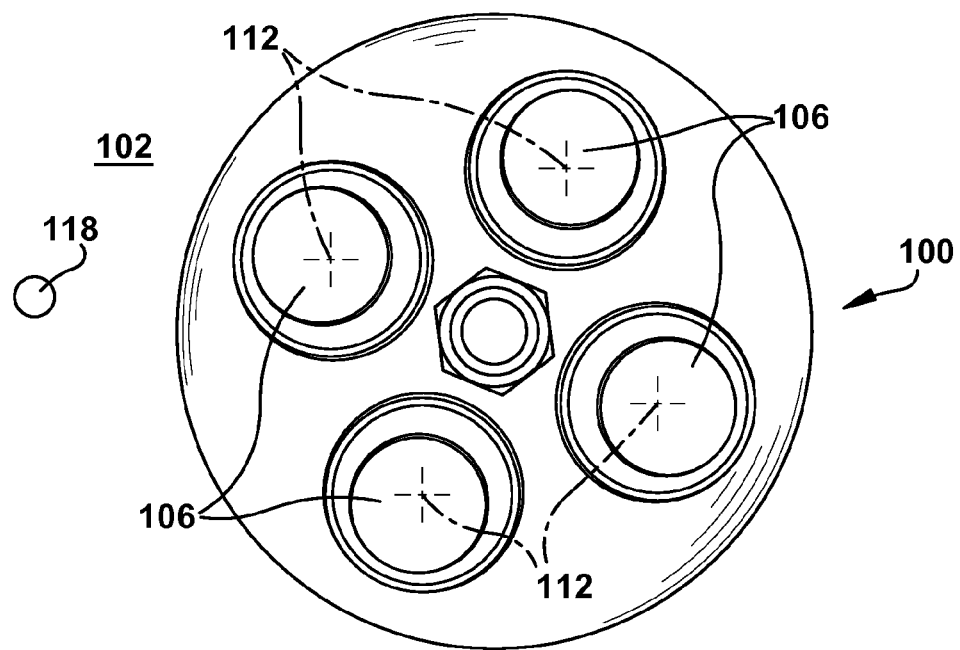
FIG. 1A is a top schematic view of an example prosthetic implant component for an embodiment of the present invention.
Figure 1B:
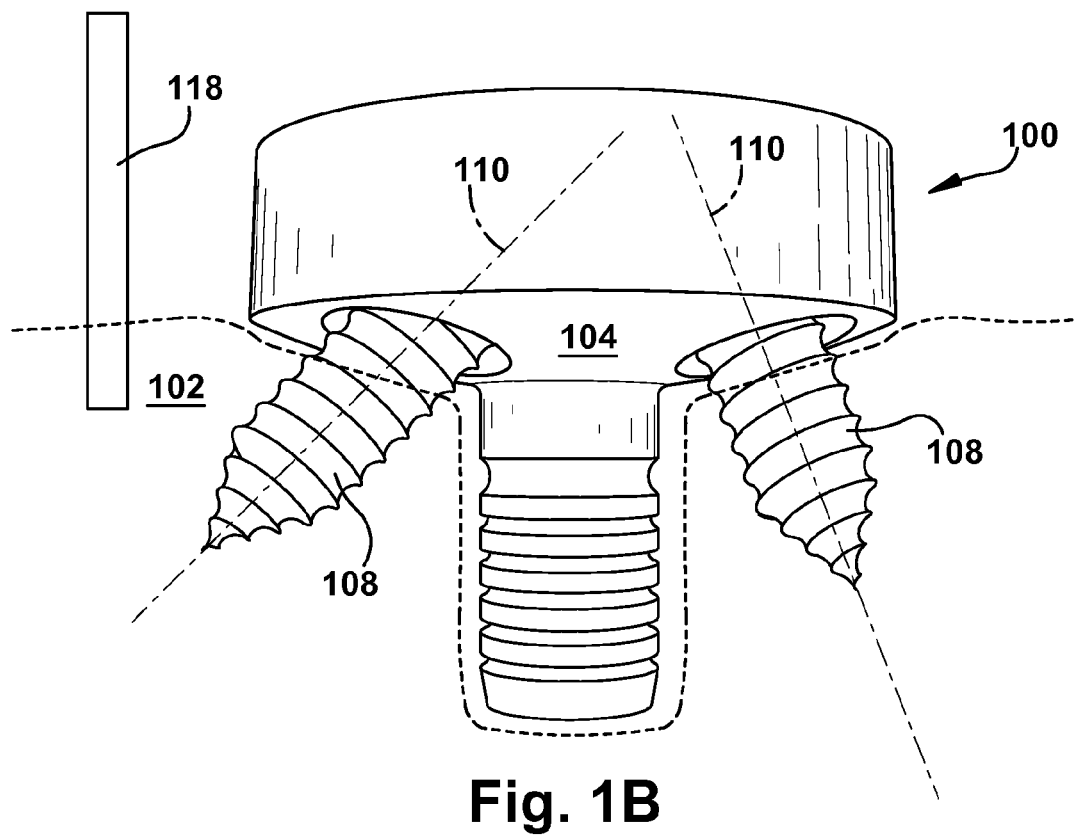
FIG. 1B is a side schematic view of the example prosthetic implant component of FIG. 1A in an example use environment.

FIGS. 1A and 1B depict top and side views, respectively, of a prior art metaglene implant 100 which is implanted into a glenoid of a patient's scapula during a reverse shoulder joint replacement procedure. The patient tissue 102 is shown and described herein at least as a scapula and the prosthetic implant component is shown and described herein at least as a metaglene prosthetic shoulder component, but the patient tissue and corresponding prosthetic implant component could be any desired types such as, but not limited to, hip joints, shoulder joints, knee joints, ankle joints, phalangeal joints, metatarsal joints, spinal structures, long bones (e.g., fracture sites), or any other suitable patient tissue 102 use environment for the present invention.

The metaglene implant 100 shown in FIGS. 1A and 1B includes a tissue-contacting surface 104 and a plurality of fastener apertures 106 which are associated with the tissue-contacting surface and are provided to assist with installation of the metaglene implant 100 upon the patient tissue 102 surface (which may be in a native/original condition or have been previously machined or altered). When the metaglene implant 100 is installed in a desired orientation relative to the patient tissue 102, at least one fastener 108 is passed through a fastener aperture 106 of the metaglene implant and is used to secure the metaglene implant to the patient tissue in a known manner. Each fastener 108 has an associated predetermined insertion trajectory 110 and a predetermined insertion location 112, which may be determined pre- or intraoperatively. Here, the predetermined insertion trajectory 110 and predetermined insertion location 112 both directly correlate with a desired installation position of a fastener 108 with respect to both the patient tissue 102 surface and the metaglene implant 100. While the insertion trajectory 110 and insertion location 112 are discussed herein as being used to aid in the insertion of a fastener 108 into the patient tissue 102, a user may wish to dictate the insertion trajectory and/or insertion location of a tool, marking device, guide pin, landmark, or any other suitable structure, elongate or not, with respect to the patient tissue for any reason and at any time during a surgical procedure, and the present invention may be used in any of these, and any other suitable, use environments and/or purposes.

At least one of the predetermined insertion trajectory 110 and predetermined insertion location 112 may be preoperatively determined responsive to preoperative imaging of the patient tissue 102 surface. Examples of suitable preoperative determinations of an insertion trajectory 110 and/or insertion location 112 are disclosed in co-pending U.S. patent application Ser. No. 13/282,550, filed 27 Oct. 2011 and titled "System of Preoperative Planning and Provision of Patient-Specific Surgical Aids", the entire contents of which are incorporated herein by reference.

Another example of suitable preoperative determination (and/or confirmation) of an insertion trajectory 110 and/or insertion location 112 for a directed structure involves the provision of a three-dimensional (physical) model of at least a portion of the patient tissue 102 surface. For example, a three-dimensional model of a patient's scapula could be provided in any suitable manner, and the metaglene implant 100 can be placed into a desired orientation with respect to the model. Fasteners 108 can be placed into desired orientations with respect to the model and the metaglene implant, via eyeballing, trial-and-error, or any other placement method, and the resultant insertion trajectory 110 and/or insertion location 112, can be used as the predetermined insertion trajectory and predetermined insertion location for the present invention.

As shown in FIG. 1B, the metaglene implant 100 may include a stem 114 which is received in a stem aperture 116 in the patient tissue 102. The stem 114 shown in FIG. 1B comprises a portion of an underside surface of the metaglene implant 100, this underside being a surface that will contact the patient tissue 102 once the metaglene implant is installed in the patient. The stem aperture 116 may be provided in any suitable manner such as, for example, with the aid of a device like those disclosed in co-pending U.S. patent application Ser. No. 13/282,509, filed 27 Oct. 2011 and titled "System and Method for Association of a Guiding Aid with a Patient Tissue", the entire contents of which are incorporated herein by reference. Optionally, and as shown in FIGS. 1A and 1B, a guide pin 118 may be associated with the patient tissue 102 in any suitable manner for use as a reference landmark, as will be discussed below.

The fasteners 108 shown in FIG. 1B are screw-type fasteners and may be self-tapping (placed into the patient tissue 102 without a pilot/pre-drilled hole) or may be inserted into pre-drilled holes which were previously prepared with the desired insertion trajectory 110 and insertion location 112. Any type or combination of fastener(s) or other elongate or non-elongate structures could be brought into contact with the surface of the patient tissue 102, whether or not penetration/insertion occurs, at the same time or at different times, with the aid of the present invention. For ease of reference, the below description uses the term "directed structure" to reference an elongate or non-elongate tissue modification tool, marking tool, fastener, and/or landmarking structure that is brought into contact with the surface of the patient tissue 102, whether or not penetration/insertion occurs.

Figure 2:
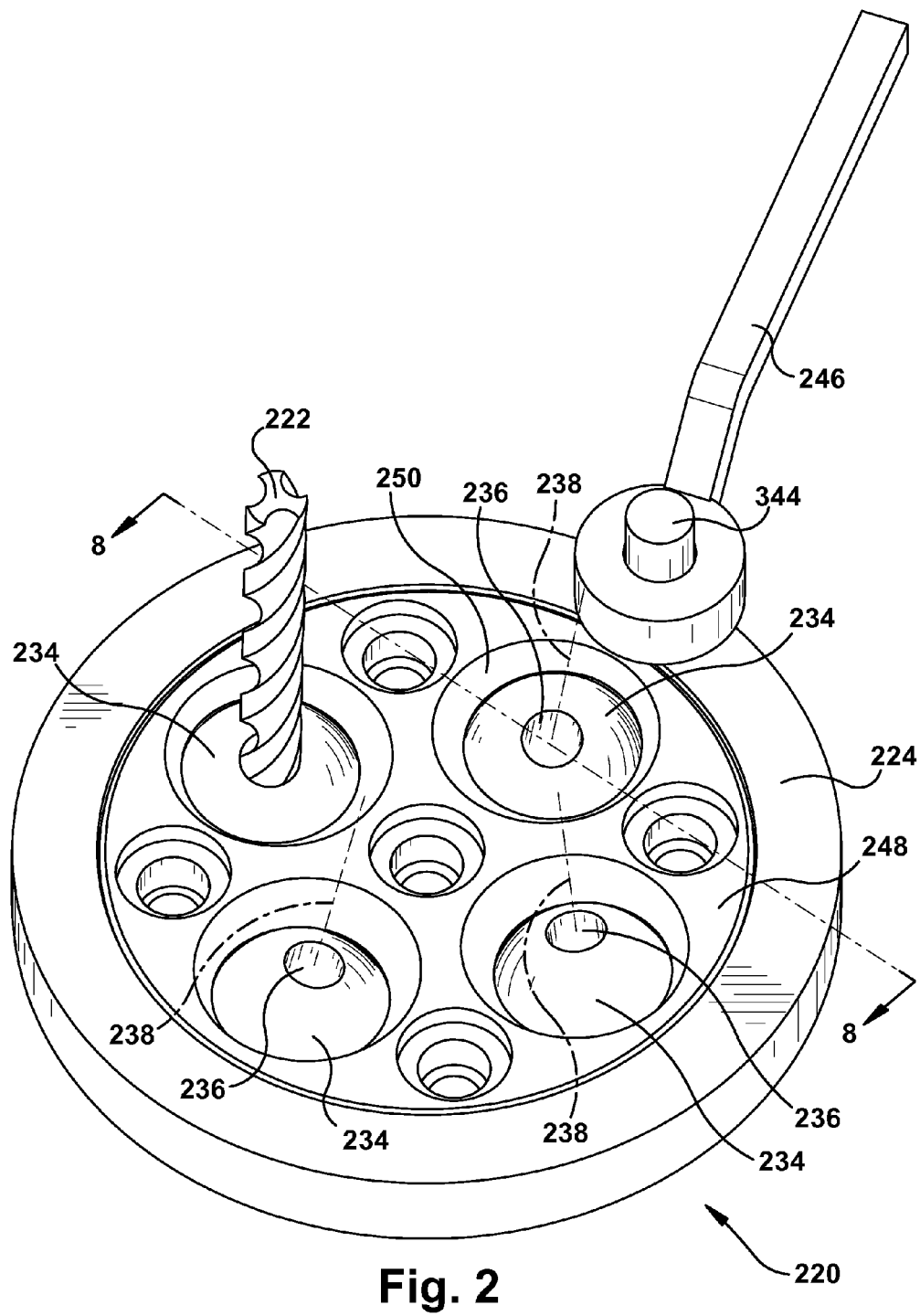
FIG. 2 is a top perspective view of an embodiment of the present invention.

In accordance with the present invention, FIG. 2 depicts a first embodiment of a directed structure placement guide 220 for assisting with positioning at least one directed structure 222, such as the drill bit shown in the Figure, in at least one of a predetermined insertion trajectory 110 and a predetermined insertion location 112 with respect to a patient tissue 102 surface. The guide 220 may be used during preparation of the patient tissue 102 surface to receive a prosthetic implant of a suitable type. In FIG. 2, the patient tissue 102 surface would be below the depicted guide 220 in the orientation shown, and the directed structure 222 embodies the insertion trajectory 110.

Figure 3:
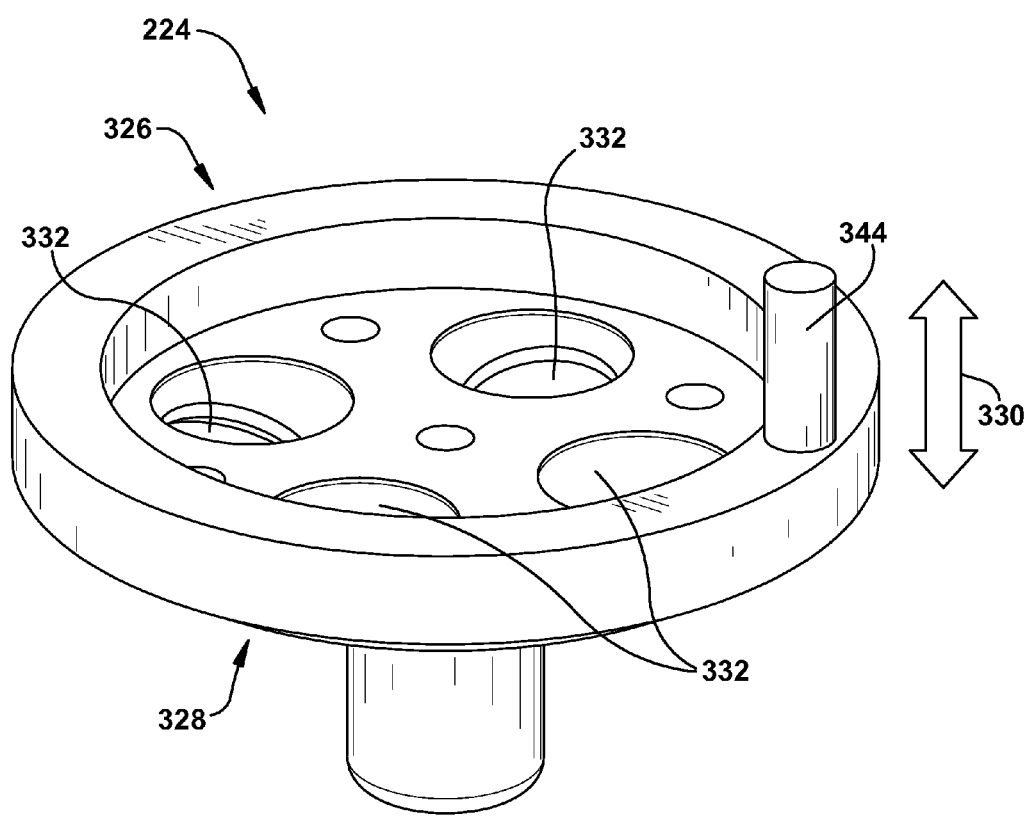
FIG. 3 is a top perspective view of a component of the embodiment of FIG. 2.

A guide base 224 of the guide 220 is shown in more detail in FIG. 3. The guide base 224 has longitudinally opposed proximal and distal base surfaces 326 and 328, respectively. (The longitudinal direction is substantially shown in FIG. 3 by direction arrow 330.) A plurality of coarse location apertures 332 extend longitudinally between the proximal and distal base surfaces 326 and 328, with the distal base surface being substantially located on the underside of the guide base 224, in the orientation of FIG. 3. Each coarse location aperture 332 substantially corresponds to a desired coarse (i.e., low-resolution or approximate) location for the directed structure with respect to the patient tissue 102 surface. In other words, while the coarse location apertures 332 do not exactly specify the desired insertion location(s) 112 for most embodiments of the present invention, the coarse location apertures each bear an approximate or "rough" correlation to the positions of the fastener apertures 106 of the metaglene implant 100 and therefore can provide an initial, coarse locating function to the directed structure 222 during use of the guide 220. The distal base surface 328 is, during use, substantially located nearer to the patient tissue 102 surface than is the proximal base surface 326.

The distal base surface 328 may mimic the structure of at least a portion of a tissue-contacting surface of the implant. The term mimic is used herein to indicate that at least a portion of the distal base surface 328 closely imitates or simulates at least a portion of the tissue-contacting surface of the implant. For example, the distal base surface 328 may mimic the footprint and/or the structure of at least a portion of the metaglene implant 100, as shown in the Figures. A comparison of FIGS. 1A-1B (showing the metaglene implant 100) and FIGS. 3-4 (showing the guide 220) reveals that the substantially round footprint, or silhouette, and stem 114 of the metaglene implant 100 are mimicked by the structure of the distal base surface 328. In other words, at least a portion of the tissue-contacting surface of the metaglene implant 100 has a predetermined three-dimensional profile (here, a slightly convex rounded shape with an extending stem 114), and a corresponding portion of the distal base surface 328 has substantially the same predetermined three-dimensional profile. Because of this mimicking, the guide 220 can be employed in the use environment of the metaglene implant 100 to guide at least one directed structure 222 in a substantially accurate manner to assist with implantation of the metaglene implant reflecting a preoperative plan. Optionally, the distal base surface 328 may contact the patient tissue 102 surface and/or some surface of the metaglene implant 100 during use of the guide 220.

Returning to FIG. 2, at least one guide sphere 234 (four shown) serves as an insertion guiding structure and has a guide bore 236 extending therethrough, the guide bores each defining a trajectory path 238 substantially longitudinally therethrough. The guide bores 236 may be configured to slidably and guidably accept a directed structure 222. Each guide sphere 234 corresponds with a different selected coarse location aperture 332, and at least a portion of each guide sphere may be located within the corresponding coarse location aperture. Each guide sphere 234 may be substantially rigid or may be made of a compliant/resilient material.

Figure 5:
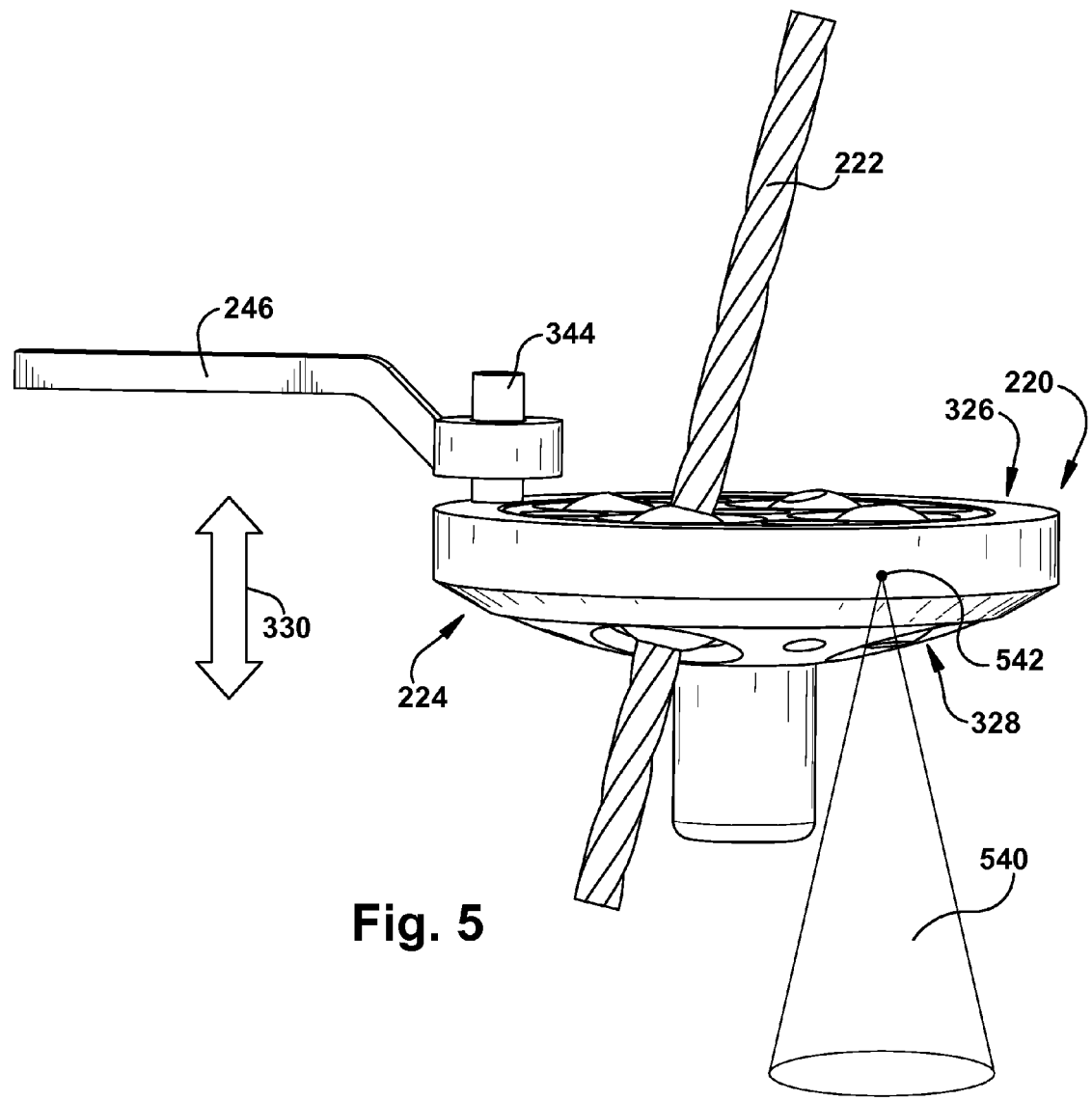
FIG. 5 is a side view of the embodiment of FIG. 2.

Each guide sphere 234 is movable with respect to its corresponding coarse location aperture 332 to precess the trajectory path 238 within a substantially conical area 540 located longitudinally distally of the distal base surface 328, as shown in FIG. 5. The conical area 540 has an apex 542 located either within or proximal to the corresponding coarse location aperture 332. In other words, the guide sphere 234 can rotate and/or roll in place, staying relatively stationary with respect to the guide 220 but changing the orientation or "pointing" direction of the guide bore 236. In this manner, the trajectory path 238 can be adjusted via manipulation of the guide sphere 234 to pass through the coarse location aperture 332 at a desired fine location. The fine, or high-resolution, location is a point within the coarse location aperture 332 at which the trajectory path 238 intersects the plane defined by the coarse location aperture. The desired fine location is indicative of the predetermined insertion location 112 of the directed structure 222 into the patient tissue 102 surface. That is, while the fine location might not be superimposed upon the insertion location 112 (due to the longitudinal spacing between the patient tissue 102 surface and the coarse location aperture 332), the trajectory path 238 links the insertion location and the fine location when the guide sphere 234 is adjusted accordingly. When the trajectory path 238 is adjusted as described, the trajectory path will indicate the desired insertion trajectory 110, as well as the desired insertion location 112. Some embodiments of the present invention are agnostic as to insertion trajectory 110, but specification of an insertion location 112 will be desirable for most embodiments of the present invention.

Optionally, and as shown in FIG. 3, a rotation feature 344 may be provided to the guide base 224. When present, the rotation feature 344 (shown here as a rotation pin) may be used in conjunction with a rotation arm 246 (which may be adjustable or fixed with respect to the guide base 224) to help place the guide 220 into a desired rotational orientation with respect to the patient tissue 102 surface. More specifically, the rotation arm 246 can be placed into a desired orientation with respect to the guide base 224. When the distal base surface 328 is placed into contact with the patient tissue 102 surface at a desired location, the guide 220 can be adjusted to place the rotation arm 246 into a predetermined relationship with an adjacent guide pin 118 to indicate that the guide 220 has reached a desired orientation with respect to the patient tissue 102 surface. For example, the guide 220 can be placed atop the patient tissue 102 surface with the protruding "stem" portion of the distal base surface 328 received in a predrilled stem aperture 116, and the guide can then rotate around the "axis" of the stem portion to achieve the predetermined relationship between the rotation arm 246 and the guide pin 118.

With reference to FIG. 2, a guide retainer 248 having a plurality of retainer apertures 250 may be provided to the guide 220 in order to help maintain the guide spheres 234 in their positions with respect to the guide base 224. Each retainer aperture 250 corresponds with a different selected guide sphere 234. The guide spheres 234 are substantially longitudinally interposed between the guide base 224 and the guide retainer 248 such that each guide sphere is sandwiched between a coarse location aperture 332 and a retainer aperture 250. It is contemplated that, for most embodiments of the present invention, the coarse location aperture 332 and retainer aperture 250 are both smaller than the maximum diameter of the guide sphere 234, to prevent the guide sphere from passing through either of these adjacent apertures.

The guide retainer 248 is longitudinally movable between loose and tight retainer positions in order to permit and restrict, respectively, movement of the guide spheres 234. When in the tight retainer position, the guide retainer 248 exerts longitudinal compressive force upon the guide spheres 234, thus "squeezing" the guide spheres 234 to maintain position and/or orientation of the guide spheres with respect to the guide base 224. Conversely, when the guide retainer 248 is in the loose retainer position, the guide spheres can be moved (i.e., rotated or rolled) with respect to the guide base 224 in order to precess the trajectory paths 238 relatively freely. As shown in the Figures, the guide retainer 248 may be located longitudinally proximally of the proximal base surface 326.

Figure 4:
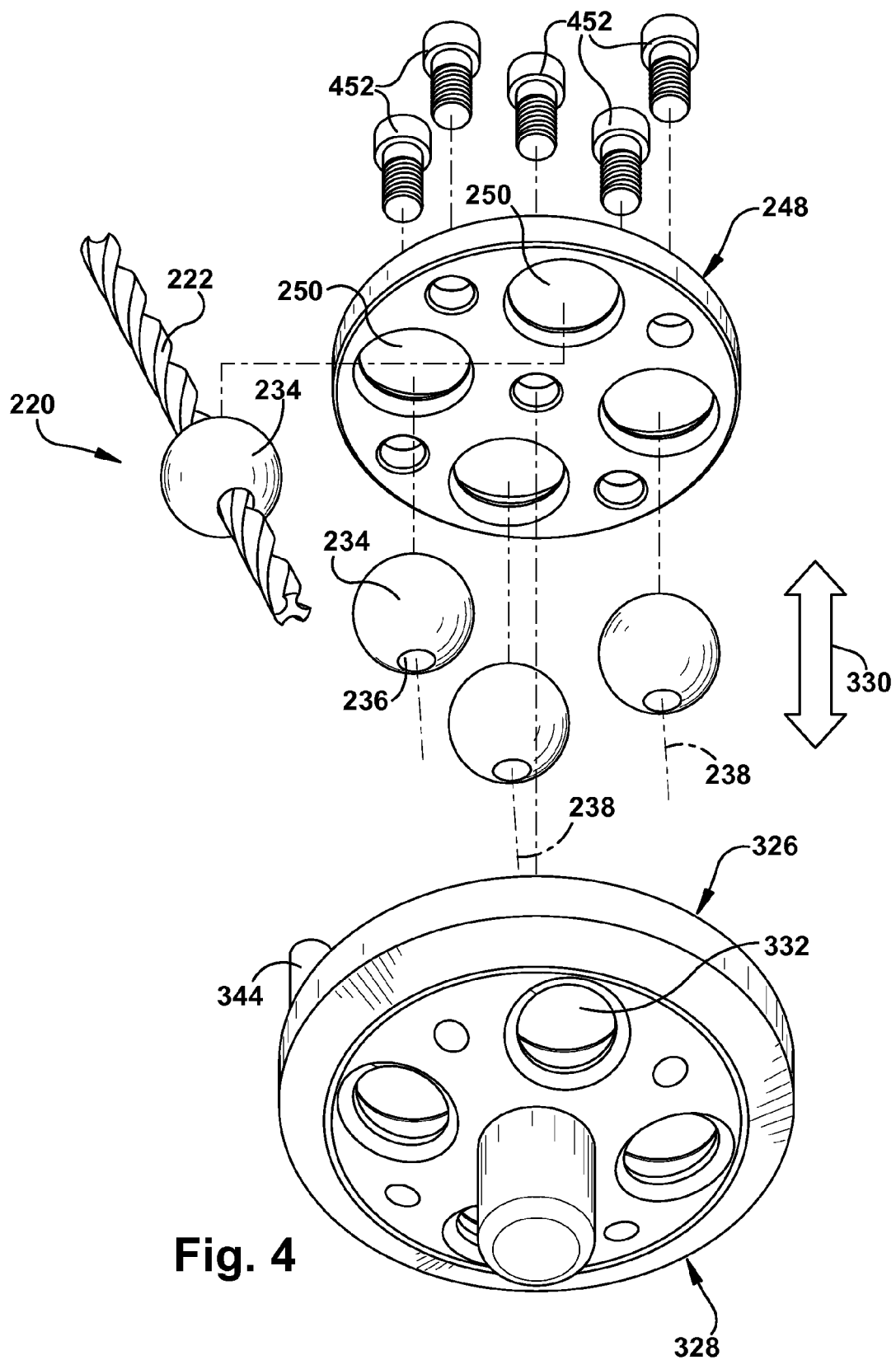
FIG. 4 is an exploded bottom view of the embodiment of FIG. 2.

FIG. 4 depicts an exploded view of the guide 220 (with the directed structure 222 and associated guide sphere 234 moved laterally out of position, for clarity of depiction). In this Figure, a plurality of retainer fasteners 452 are shown proximal of the guide retainer 248. In the assembled guide 220, the retainer fasteners 452 pass through the guide retainer 248 and engage the guide base 224 to hold the guide retainer to the guide base. Particularly when the retainer fasteners 452 are longitudinally adjustable (e.g., threaded screws), the retainer fasteners may be tightened to clamp down on the guide retainer 248 to hold the guide retainer in the tight position.

Figure 6:
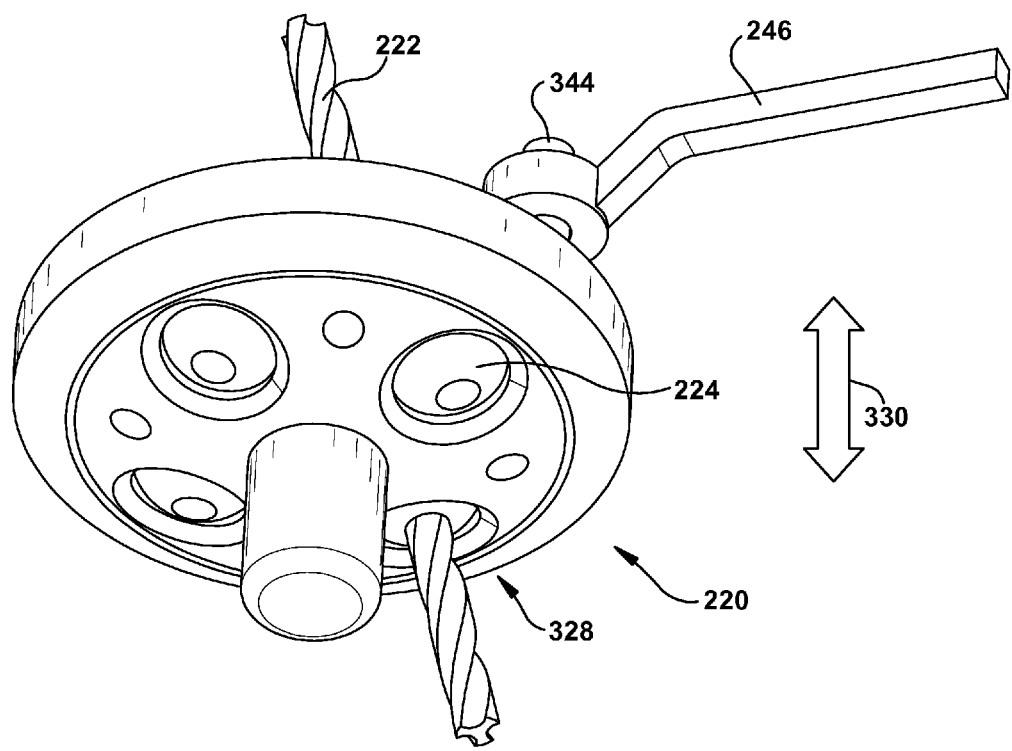
FIG. 6 is a bottom perspective view of the embodiment of FIG. 2.
Figure 7:
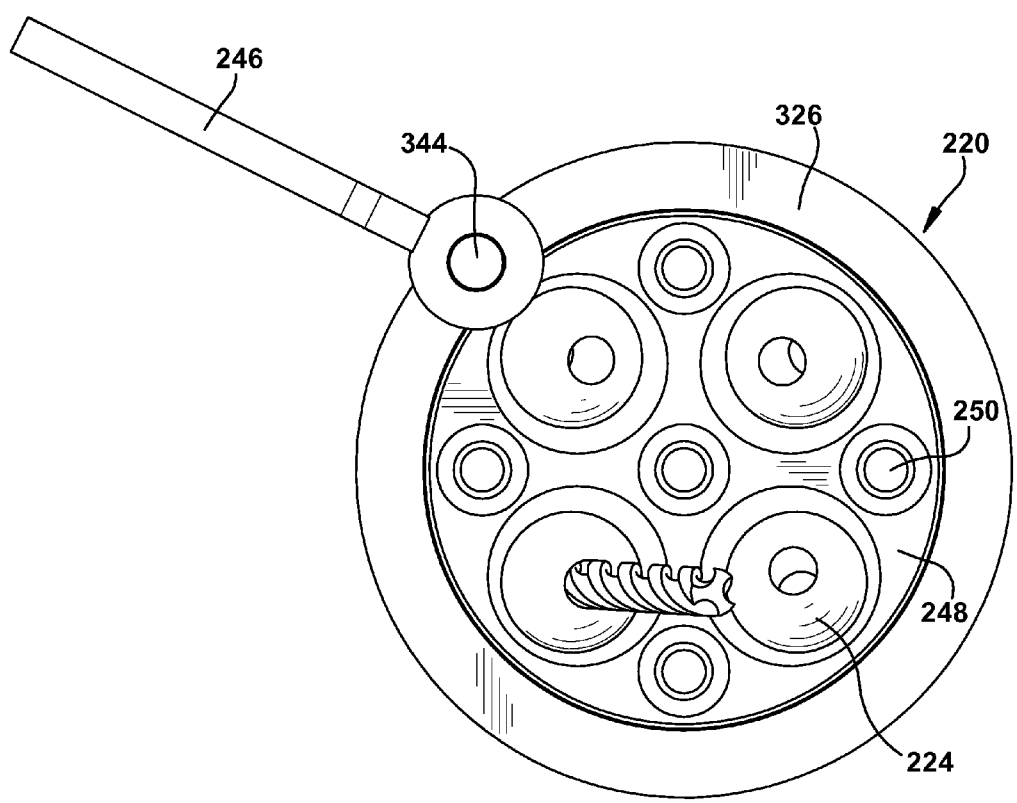
FIG. 7 is a top view of the embodiment of FIG. 2.

FIGS. 6 and 7 show bottom and top views, respectively, of the assembled guide 220, including a guide base 224, a plurality of movable/adjustable guide spheres 234, a guide retainer 248, and a rotation feature 344 with an associated rotation arm 246. The retainer fasteners 452 are omitted from these Figures, for clarity of depiction, but would normally be located in the retainer apertures 250 when the guide retainer 248 is in the tight position.

Figure 8:
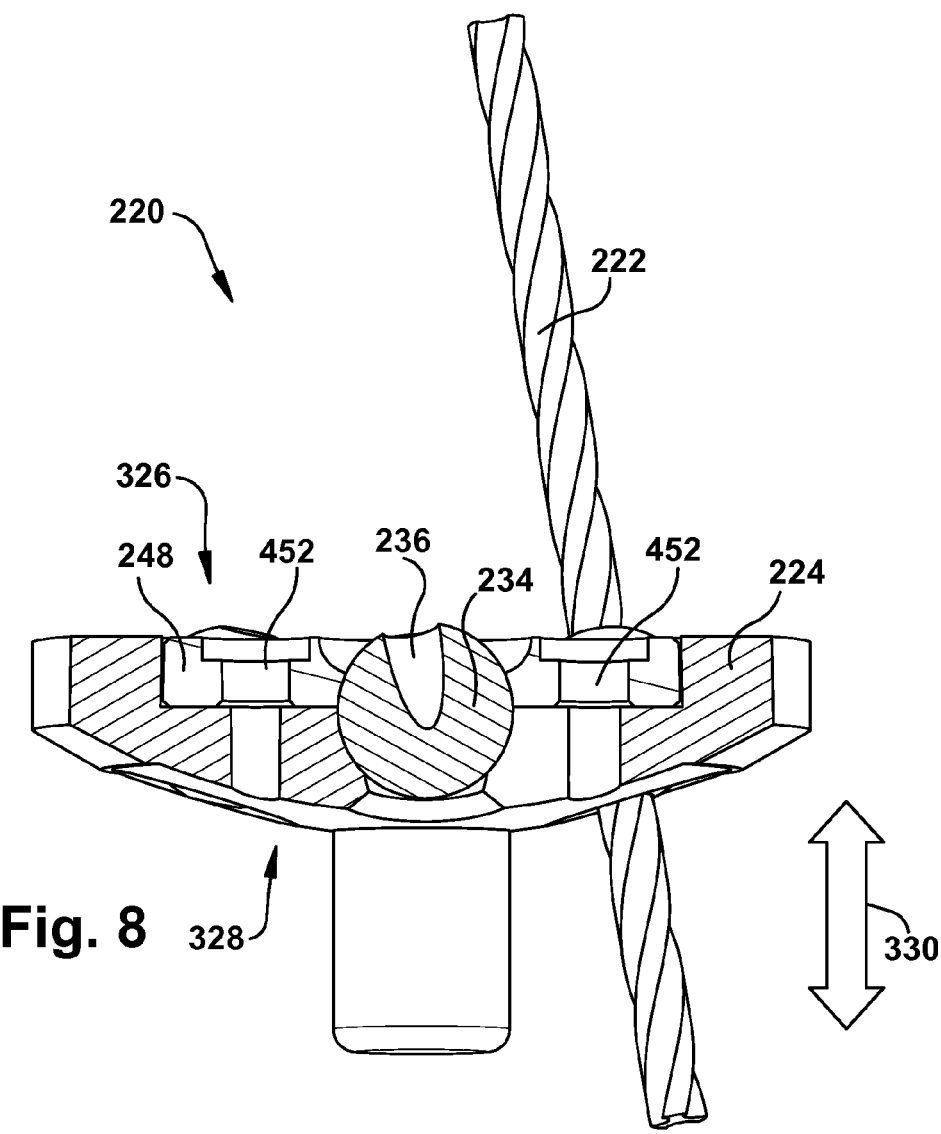
FIG. 8 is a cross-sectional view taken along line 8-8 of FIG. 2.

FIG. 8 is a cross-sectional view taken along line 8-8 of FIG. 2. In FIG. 8, the longitudinal arrangement of the guide base 224, guide spheres 234, guide retainer 248, and retainer fasteners 452 is shown. In this configuration, the guide retainer 248 can be removed entirely in the proximal direction from the guide base 224, if desired, upon removal of the retainer fasteners 452. Alternately, the retainer fasteners 452 can be merely adjusted to move the guide retainer 248 between the tight and loose retainer positions.

Figure 9:
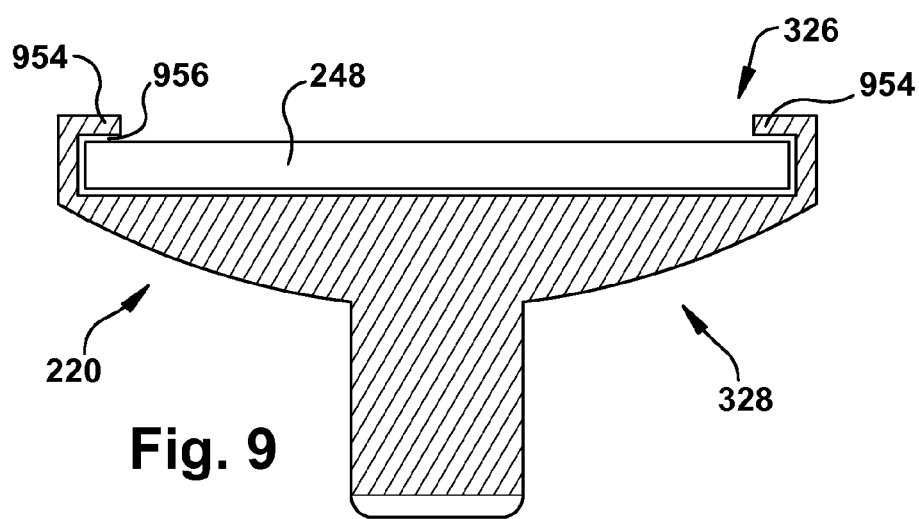
FIG. 9 is an alternate schematic configuration of the cross-sectional view of FIG. 8.

Conversely, and as shown schematically in FIG. 9, the guide base 224 can include a retaining rim 954 extending around at least a portion of the perimeter of the proximal base surface 326. When present, the retaining rim 954 may be longitudinally spaced from another portion of the proximal base surface 326 to define a retainer gap 956 therebetween, with at least a portion of the guide retainer 248 being located in the retainer gap (i.e., longitudinally between the retaining rim 954 and another portion of the proximal base surface 326). In this manner, the guide retainer 248 can be substantially restricted from longitudinal movement further proximally from the guide base 224 than when the guide retainer is in the loose retainer position. In other words, in the configuration of FIG. 9, the retainer fasteners 452 can be removed completely from the remaining portions of the guide 220, but the retaining rim 954 will prevent the guide retainer 248 from coming apart from the rest of the guide 220.

In use, a guide 220 should be selected which has a distal base surface 328 mimicking the tissue-contacting surface of an implant to be installed into the patient's body. The guide retainer 248 is placed in the loose retainer position and each guide sphere 234 is manipulated to place the trajectory path 238 into the predetermined insertion trajectory 110 such that the trajectory path intersects the coarse location aperture 332 at the desired fine location—this will automatically and concurrently place the trajectory path into an appropriate orientation to intersect the patient tissue 102 surface at the predetermined insertion location 112 when the guide 220 is placed in the correct position on the patient tissue surface. For example, the guide spheres 234 could be "rolled" within the coarse location apertures 332 until the guide bores 236 achieve a predetermined position with respect to the guide base 224. When present, the rotation arm 246 can be adjusted as desired.

Figure 10A:
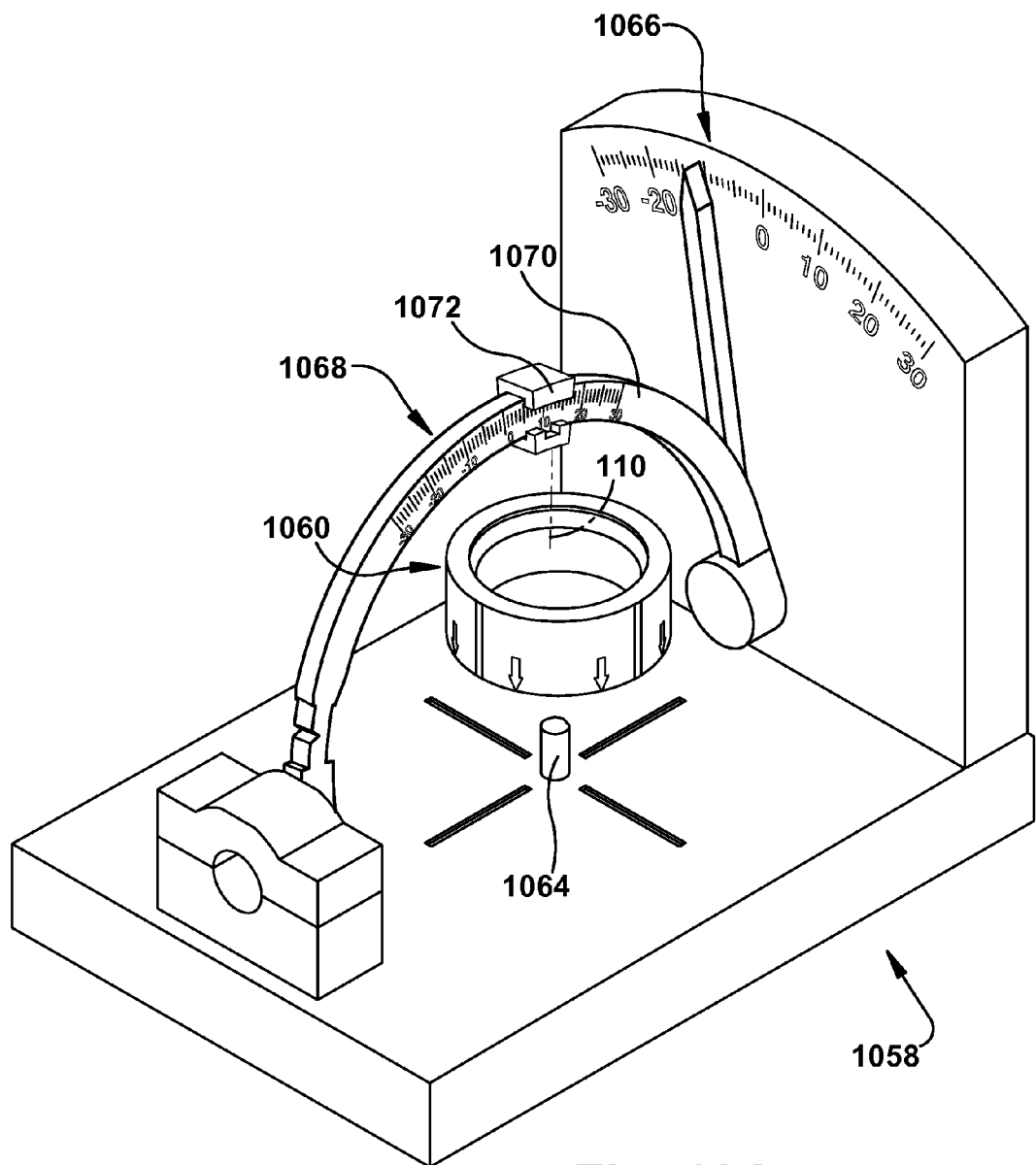
FIG. 10A is a perspective side view of a device for use with the embodiment of FIG. 2.
Figure 10B:
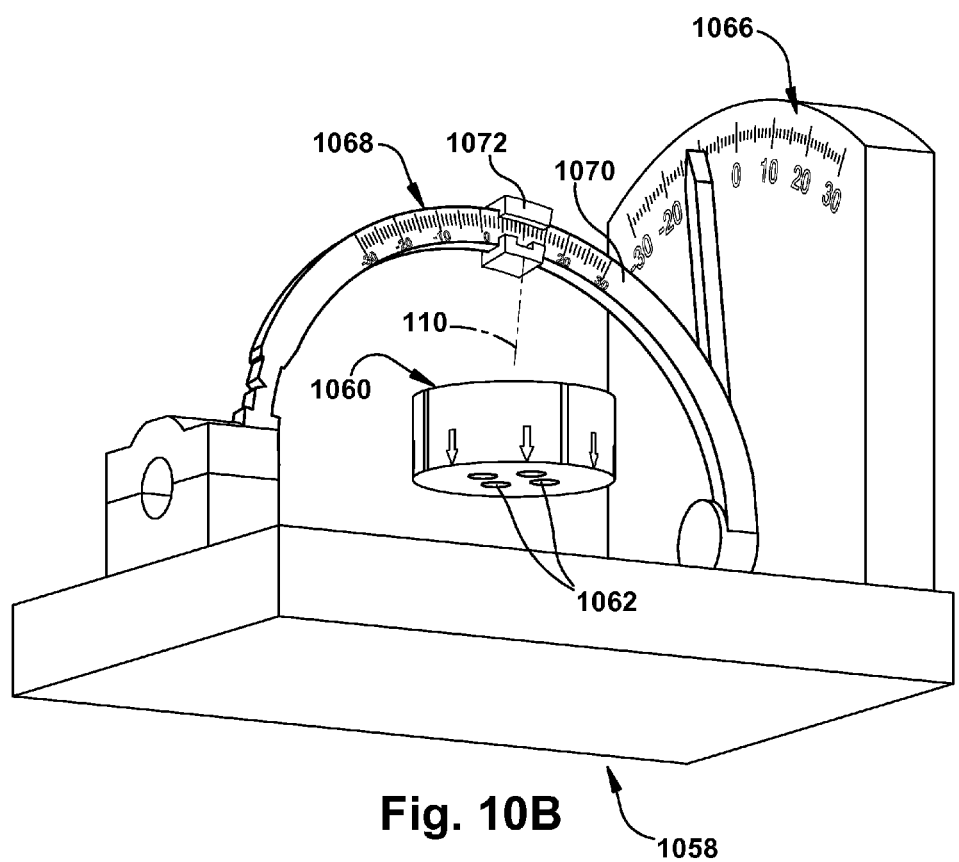
FIG. 10B is a perspective bottom view of the device of FIG. 10A.

The described adjustments can occur in any suitable manner. For example, a user could "eyeball" or approximate the movement of the guide spheres 234. As another example, a preoperative planning system could output numerical values for the guide sphere locations—this option would require that a scale or other indicator of position be provided to transfer the values to the guide 220—a suitable goniometer 1058 for setting the guide 220 is shown in FIGS. 10A and 10B. Here, a carriage 1060 (shown removed from the rest of the goniometer 1058 for clarity) acts to receive the distal base surface 328 of the guide 220 to hold the guide steady for setting of at least one of the insertion trajectory 110 and the insertion location 112. When the guide 220 is held in the carriage 1060, a selected one of several locating holes 1062 on the underside of the carriage—shown in FIG. 10B—is mated with a locating stud 1064 on a base of the goniometer 1058. Two setting scales 1066 and 1068 are used to set an orientation of a rotating arch 1070 and a guiding block 1072, respectively, according to predetermined numerical values. Though it is not visible in these Figures, the guiding block 1072 has a throughbore configured to guide a directed structure 222 therethrough along a desired insertion trajectory 110. The rotating arch 1070 and guiding block 1072 of the goniometer 1060 may be manipulated according to the predetermined numerical values to place the guiding block in a predetermined orientation (embodying the insertion trajectory 110) with respect to the guide 220 when the guide is in the carriage 1060 and the locating stud 1064 is mated with a predetermined one of the locating holes 1062. A directed structure 222 (not shown in FIGS. 10A and 10B) may then be passed through the guiding block 1072 along the insertion trajectory 110. A desired guide sphere 234 of the guide 220 being held by the goniometer 1058 can then be manipulated until the guide bore 236 lines up with, and optionally admits, the directed structure 222 being guided along the insertion trajectory 110 by the guiding block 1072.

Figure 11:
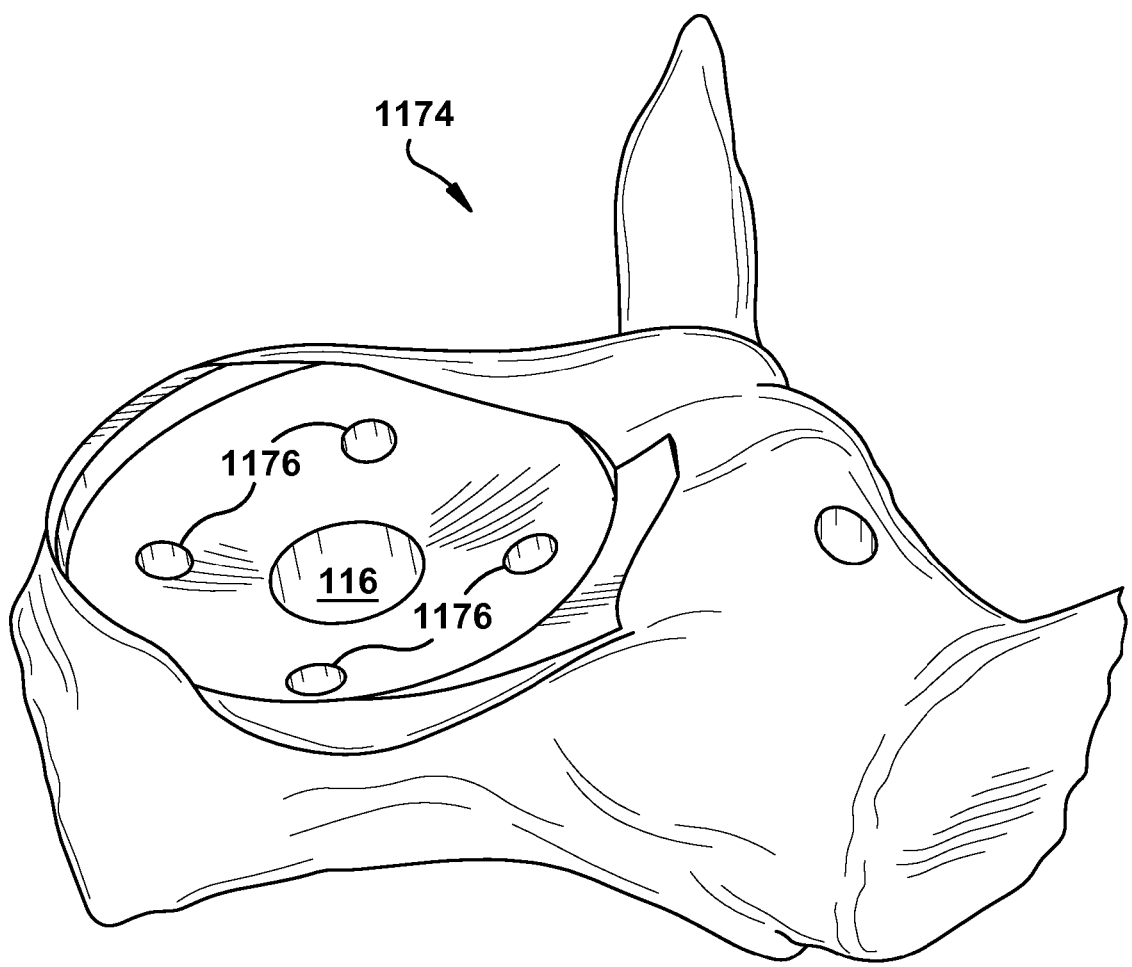
FIG. 11 is a perspective top view of a device for use with the embodiment of FIG. 2.

As another option for setting at least one of the desired insertion trajectories 110 and insertion locations 112, a three-dimensional model 1174 of the patient tissue 102, shown in FIG. 11, could be used to set the guide 220. In this example, the three-dimensional model 1174 might embody desired insertion trajectories and locations 110 and 112, such as via the cavities 1176 of FIG. 11, which may be produced by any suitable means, including, but not limited to, preoperative planning/manufacture of the model and dead reckoning or "eyeballing" by the user. The guide 220 may be placed into contact with the three-dimensional model 1174 with at least one of these placed example directed structures 222 extending through a corresponding guide bore 224. (Optionally, the example directed structures 222 may be temporarily removed from the three-dimensional model 1174, their cavities 1176 remaining in the model as shown in FIG. 11, so that the guide 220 can be placed on the model, then the example directed structures can be re-inserted through the guide, such as through the guide bores 236, and into the cavities.) Once the guide spheres 234 have been adjusted to reflect the insertion trajectories and locations 110 and 112 of the example directed structures 222 with respect to the three-dimensional model, the guide retainer 248 is moved from the loose retainer position to the tight retainer position, and the example directed structures may be removed from the guide bores 236, with their predetermined insertion locations and trajectories maintained by the guide 220. The guide 220 can then be removed from the three-dimensional model 1174 of the patient tissue 102 and placed into contact with the actual patient tissue 102, in a position substantially corresponding to the position the guide previously held upon the three-dimensional model 1174, to transfer at least one of the predetermined insertion location(s) and predetermined insertion trajectory(ies) to the patient tissue surface.

Regardless of how the guide spheres 234 are manipulated to reflect the predetermined insertion trajectories and locations 110 and 112, the guide retainer 248 may be moved to the tight retainer position to maintain the guide spheres in the "pre-set" position, which could also be considered a guiding orientation/configuration. The guide 220 is then placed into a position with respect to the patient tissue 102 surface in which the predetermined insertion trajectories and locations 110 and 112 may be provided to the patient tissue surface. For example, the distal base surface 328, or any other portion of the guide 220, may be placed into contact with the underlying patient tissue 102 surface or in contact with a previously placed metaglene implant 100. When present, the rotation arm 246 can be placed into contact with a guide pin 118 in a predetermined orientation, as previously mentioned, to set and/or confirm the rotational position of the guide 220 with respect to the patient tissue 102.

Once the guide 220 has been adjusted into the guiding configuration and positioned appropriately with respect to the patient tissue 102, a directed structure 222 can pass slidably through each guide bore 236 and into contact—optionally penetrating contact—with the patient tissue 102 surface. The guide bores 236 will guide the corresponding directed structures 222 into contact with the patient tissue 102 surface at the predetermined insertion locations 112. When the directed structures 222 penetrate into the patient tissue 102, the guide bore 236 guide such penetration along the predetermined insertion trajectories 110. When such penetration is performed, the directed structures 222 may each create an aperture in the patient tissue 102. The configuration of these apertures may be based upon a preoperatively determined plan to install the implant into a predetermined implant orientation with respect to the patient tissue surface. In the example embodiment of FIGS. 1-9, the metaglene implant 100 has four fasteners 108 which each should be installed at predetermined insertion trajectories and locations 110 and 112, and the guide 220 can be used to direct a drill bit and/or the fasteners themselves into those predetermined insertion trajectories and locations.

Once the predetermined insertion trajectories and locations 110 and 112 have been transferred to the directed structures 222 in a desired manner, the guide 220 can be removed from the patient tissue 102 surface and the surgical procedure can proceed. The guide 220 can be cleaned and sterilized and otherwise readied for use as an aid to transfer predetermined insertion trajectories and locations 110 and 112 in another patient.

FIGS. 12-16 depict a guide 220' according to a second embodiment of the present invention. The guide 220' of FIGS. 12-16 is similar to the guide 220 of FIGS. 1-11 and therefore, structures of FIGS. 12-16 that are the same as or similar to those described with reference to FIGS. 1-11 have the same reference numbers with the addition of a "prime" mark. Description of common elements and operation similar to those in the previously described first embodiment will not be repeated with respect to the second embodiment.

Figure 12:
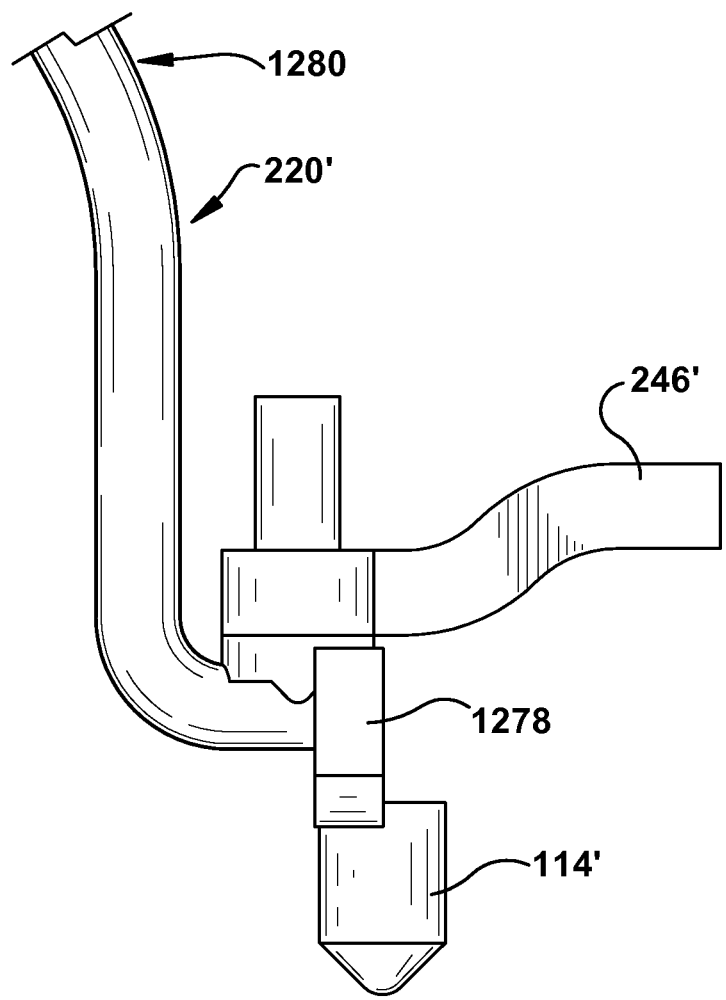
FIG. 12 is a partial side view of an embodiment of the present invention.
Figure 13:
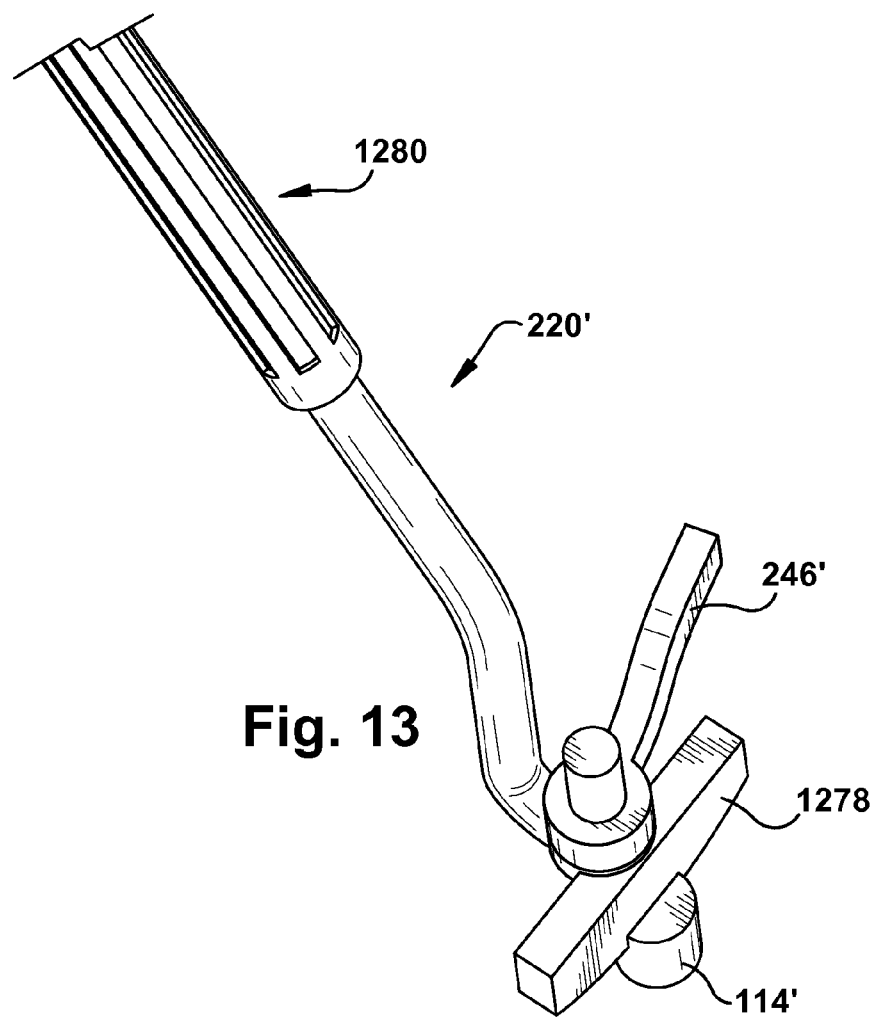
FIG. 13 is a partial perspective top view of the embodiment of FIG. 12.

FIGS. 12 and 13 are partial side and top views, respectively, of a bone scribe type guide 220' which can be used to direct landmarking of a patient tissue 102' surface using an ink pen, bovie (for burn marking), or other marking instrument as the directed structure 222'.

Figure 14:
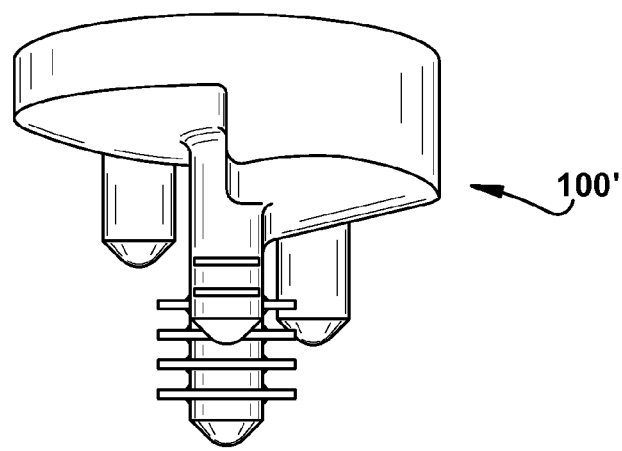
FIG. 14 is a side view of an prosthetic implant component for use with the embodiment of FIG. 12.

In FIGS. 12-16, the guide 220' mimics at least a portion of the structure of a stepped-type glenoid implant 100', such as that shown in FIG. 14.

Figure 15A:
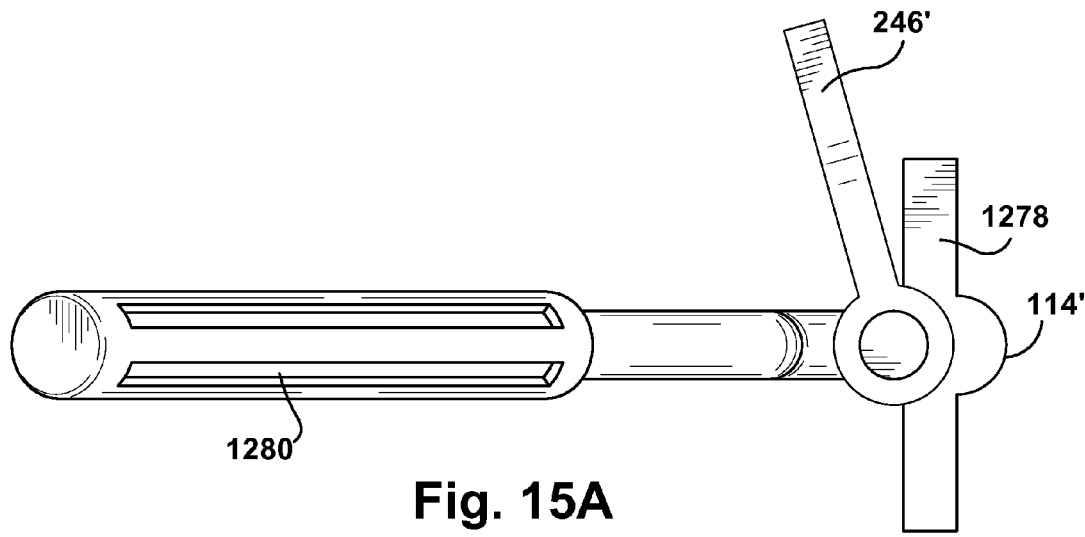
FIGS. 15A-15B are top views depicting a sequence of operation of the embodiment of FIG. 12.
Figure 15B:
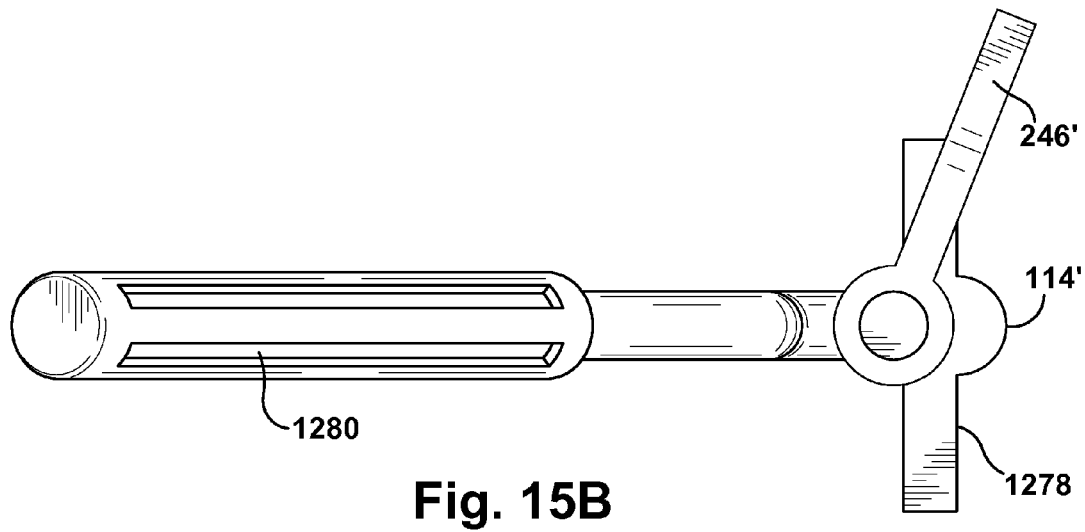

An insertion guiding structure 1278 of the guide 220' is movably supported by the guide base 224' and is adjustable into a guiding configuration in which at least one of the predetermined insertion trajectory 110' and predetermined insertion location 112' is selectively imparted to the directed structure 222'. Here, the insertion guiding structure 1278 is a planar face which indicates a centerline of the stepped-type glenoid implant. The handle 1280 may be adjustable for a particular use environment of the present invention. The rotation arm 246' is adjusted, as shown in the sequence of FIGS. 15A and 15B to embody a desired relationship with a guide pin 118' previously placed at or near the patient tissue 102' surface in order to impart a desired rotational orientation to the guide 220'.

Figure 16:
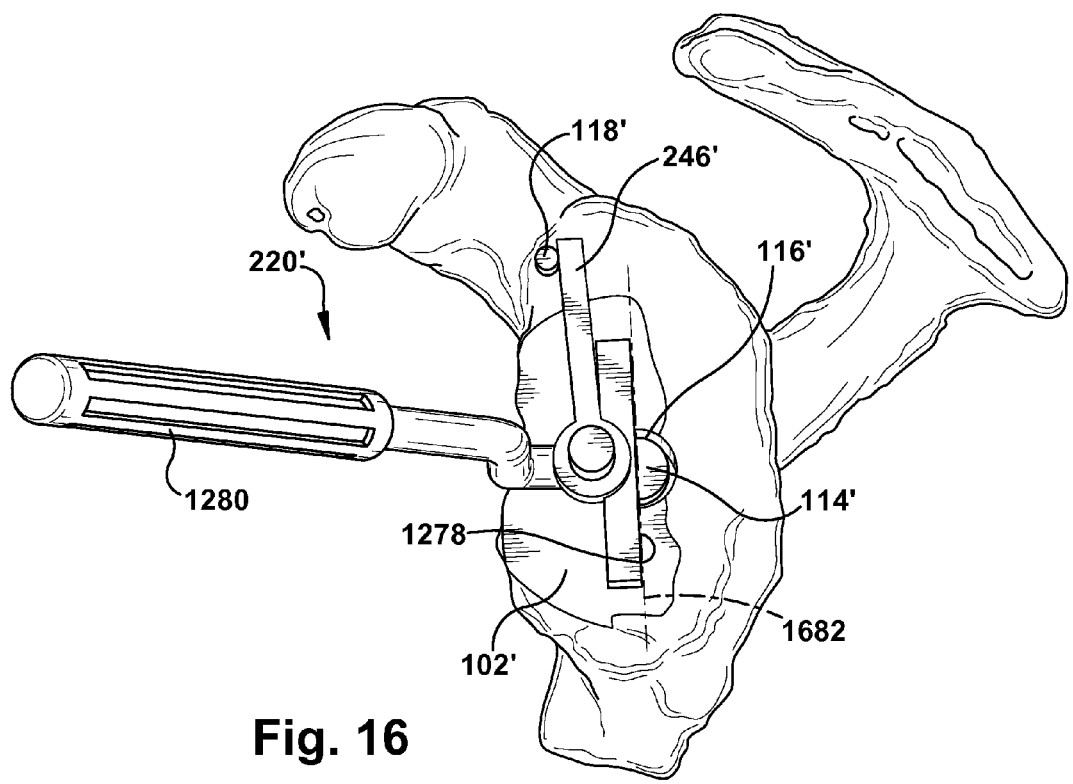
FIG. 16 is a top view of the embodiment of FIG. 12 in an example use environment.

The distal base surface 328' includes a stem-type protrusion 114' which is configured to enter a previously provided stem aperture 116' in the patient tissue 102'. Once this placement has been made, the handle 1280 may be manipulated to rotate the guide 220' until the rotation arm 246' achieves the desired relationship with the guide pin 118'. This achievement indicates that the insertion guiding structure 1278 has achieved a desired guiding orientation with respect to the patient tissue 102' surface. In many use environments of the present invention, this guiding orientation will be substantially identical to an installation orientation in which the implant is affixed to the patient tissue 102' surface. The directed structure 222' can then be guided by the insertion guiding structure 1278—e.g., a marking device can trace along the flatted side of the guide base 224'—to place a landmarking line in a desired insertion location 112' along the patient tissue 102'. FIG. 16 depicts this relationship, with the guide 220' being located at a patient tissue 102' surface and the protrusion 114' in the stem aperture 116'. Since the rotation arm 246' has been placed in contact with a previously placed guide pin 118', the user can be confident that the insertion guiding structure 1278 is located in a predetermined orientation with respect to the patient tissue 102'. A marking can be made, such as line 1682, along the insertion guiding structure 1278 and used as a later landmark on the patient tissue 102' surface.

Once the landmarking line 1682 has been inscribed on the patient tissue 102' surface, the guide 220' can be removed from the area, leaving the line as a guide for mechanical alteration of the patient tissue and/or placement of the implant upon the patient tissue.

While aspects of the present invention have been particularly shown and described with reference to the preferred embodiment above, it will be understood by those of ordinary skill in the art that various additional embodiments may be contemplated without departing from the spirit and scope of the present invention. For example, the specific methods described above for using the guide 220 are merely illustrative; one of ordinary skill in the art could readily determine any number of tools, sequences of steps, or other means/options for placing the above-described apparatus, or components thereof, into positions substantively similar to those shown and described herein. Any of the described structures and components could be integrally formed as a single piece or made up of separate sub-components, with either of these formations involving any suitable stock or bespoke components and/or any suitable material or combinations of materials; however, the chosen material(s) should be biocompatible for many applications of the present invention. The mating relationships formed between the described structures need not keep the entirety of each of the "mating" surfaces in direct contact with each other but could include spacers or holdaways for partial direct contact, a liner or other intermediate member for indirect contact, or could even be approximated with intervening space remaining therebetween and no contact. Though certain components described herein are shown as having specific geometric shapes, all structures of the present invention may have any suitable shapes, sizes, configurations, relative relationships, cross-sectional areas, or any other physical characteristics as desirable for a particular application of the present invention. The guide 220 may include a plurality of structures cooperatively forming any components thereof and temporarily or permanently attached together in such a manner as to permit relative motion (e.g., pivoting, sliding, or any other motion) therebetween as desired. Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, we claim:

1. A directed structure placement guide for assisting with positioning at least one directed structure in at least one of a predetermined insertion trajectory and a predetermined insertion location with respect to a patient tissue surface, the guide comprising:

a guide base having longitudinally opposed proximal and distal base surfaces and a plurality of coarse location apertures extending longitudinally between the proximal and distal base surfaces, each coarse location aperture substantially corresponding to a desired coarse location for the directed structure with respect to the patient tissue surface, the distal base surface being substantially located nearer to the patient tissue surface than is the proximal base surface;

a plurality of guide spheres, each guide sphere having a guide bore extending therethrough and defining a trajectory path substantially longitudinally therethrough, each guide sphere corresponding with a different selected coarse location aperture, and each guide sphere being movable with respect to the coarse location aperture to intersect the trajectory path with the coarse location aperture at a desired fine location, the desired fine location being indicative of the predetermined insertion location of the directed structure into the patient tissue surface; and a guide retainer having a plurality of retainer apertures, each retainer aperture corresponding with a different selected guide sphere, the guide spheres being substantially longitudinally interposed between the guide base and the guide retainer, the guide retainer being longitudinally movable between loose and tight retainer positions, wherein longitudinal movement of the guide retainer into the tight retainer position causes exertion of a longitudinal compressive force upon the guide spheres to maintain position of the guide spheres with respect to the guide base;

wherein each guide sphere is manipulated to place the trajectory path into the predetermined insertion trajectory at the desired fine location before the guide retainer achieves the tight retainer position and the guide bore guides a directed structure passed therethrough into contact with the patient tissue surface at the predetermined insertion trajectory and location.

2. The directed structure placement guide of claim 1, wherein at least a portion of each guide sphere is located within the corresponding coarse location aperture.

3. The directed structure placement guide of claim 1, wherein the distal base surface is placed into contact with the underlying patient tissue surface before the directed structure is passed through the guide bore.

4. The directed structure placement guide of claim 1, wherein each guide sphere is substantially rigid.

5. The directed structure placement guide of claim 1, wherein the distal base surface mimics a footprint of an implant to be fastened to the patient tissue surface, the implant having at least one fastener aperture to assist with installation of the implant upon the patient tissue surface.

6. The directed structure placement guide of claim 5, wherein each coarse location aperture corresponds to an approximate position of a selected fastener aperture of the implant.

7. The directed structure placement guide of claim 5, wherein the predetermined insertion location and predetermined insertion trajectory both directly correlate with a desired installation position of a fastener with respect to both the patient tissue surface and the implant.

8. The directed structure placement guide of claim 1, wherein the directed structure passing through the guide bore is at least one of a tissue modification tool, a marking tool, a fastener, and a landmarking structure.

9. The directed structure placement guide of claim 1, wherein at least one of the predetermined insertion location and the predetermined insertion trajectory is preoperatively determined responsive to preoperative imaging of the patient tissue surface.

10. The directed structure placement guide of claim 1, wherein at least one of the predetermined insertion location and the predetermined insertion trajectory is determined with the assistance of a three-dimensional model of at least a portion of the patient tissue surface.

11. The directed structure placement guide of claim 1, wherein the guide base includes a retaining rim extending around at least a portion of a perimeter of the proximal base surface, the retaining rim being longitudinally proximally spaced from the proximal base surface to define a retainer gap therebetween, at least a portion of the guide retainer being located longitudinally between the proximal base surface and the retaining rim such that the guide retainer is substantially restricted from longitudinal movement further proximally from the guide base than when the guide retainer is in the loose retainer position.

12. The directed structure placement guide of claim 1, wherein the guide retainer is held in the tight retainer position through action of at least one retainer fastener passing through the guide retainer and engaging the guide base.

13. A directed structure placement guide for assisting with positioning at least one directed structure in at least one of a predetermined insertion trajectory and a predetermined insertion location with respect to a patient tissue surface during preparation of the patient tissue surface to receive an implant, the implant having a tissue-contacting surface and a plurality of fastener apertures associated therewith, the guide comprising:

a guide base having a distal base surface mimicking a structure of at least a portion of the tissue-contacting surface of the implant, the guide base also having a proximal base surface longitudinally spaced from the distal base surface, a plurality of coarse location apertures extending through the guide base between the proximal and distal base surfaces, each coarse location aperture bearing a corresponding relationship to the guide base as does a selected fastener aperture to the implant;

a plurality of guide spheres, each guide sphere having a guide bore extending therethrough and configured to slidably and guidingly accept a directed structure, each guide sphere being associated with a selected coarse location aperture, and each guide bore defining a trajectory path therethrough, each guide sphere being manipulable to precess the trajectory path within a substantially conical area located longitudinally distally of the distal base surface, the conical area having an apex located a selected one of within and proximal to the selected coarse location aperture; and a guide retainer located longitudinally proximally of the proximal base surface, the guide retainer being longitudinally movable between a loose retainer position, in which the plurality of guide spheres can be moved with respect to the guide base, and a tight retainer position, in which the plurality of guide spheres are substantially prevented from movement with respect to the guide base, wherein longitudinal movement of the guide retainer into the tight retainer position causes exertion of a longitudinal compressive force upon the guide spheres to maintain position of the guide spheres with respect to the guide base;

wherein each guide sphere is manipulated to place a respective trajectory path into the predetermined insertion trajectory and at least one of the guide base and each guide sphere is manipulated to place a respective trajectory path into an interception position at the predetermined insertion location upon the patient tissue surface when the distal guide base is in contact with at least a portion of the underlying patient tissue surface, the guide retainer is moved from the loose retainer position to the tight retainer position to maintain each guide sphere with the trajectory path in the predetermined insertion trajectory and interception position, and the guide bore is configured to slidingly accept the directed structure and to guide the directed structure into contact with the patient tissue surface at the predetermined insertion location and at the predetermined insertion trajectory.

14. The directed structure placement guide of claim 13, wherein the predetermined insertion location and predetermined insertion trajectory both directly correlate with a desired installation position of a fastener with respect to both the patient tissue surface and the implant.

15. The directed structure placement guide of claim 13, wherein the directed structure passing through the guide bore is at least one of a tissue modification tool, a marking tool, a fastener, and a landmarking structure.

16. The directed structure placement guide of claim 13, wherein at least one of the predetermined insertion location and the predetermined insertion trajectory is preoperatively determined responsive to preoperative imaging of the patient tissue surface.

17. The directed structure placement guide of claim 13, wherein at least one of the predetermined insertion location and the predetermined insertion trajectory is determined with the assistance of a three-dimensional model of at least a portion of the patient tissue surface.

18. The directed structure placement guide of claim 13, wherein the guide base includes a retaining rim extending around at least a portion of a perimeter of the proximal base surface, the retaining rim being longitudinally proximally spaced from the proximal base surface to define a retainer gap longitudinally therebetween, at least a portion of the guide retainer being located longitudinally between the proximal base surface and the retaining rim such that the guide retainer is substantially restricted from longitudinal movement further proximally from the proximal base surface than when the guide retainer is in the loose retainer position.

19. The directed structure placement guide of claim 13, wherein the guide retainer is held in the tight retainer position through action of at least one retainer fastener passing through the guide retainer and engaging the guide base.

* * * * *